US00PP10042P

United States Patent [19]

Glicenstein

[11] Patent Number: Plant 10,042

[45] Date of Patent: Sep. 23, 1997

[54] CHRYSANTHEMUM PLANT NAMED 'AUTUMN KIMBERLY'

[75] Inventor: Leon Glicenstein, Salinas, Calif.

[73] Assignee: Yoder Brothers, Inc., Barberton, Ohio

[21] Appl. No.: 605,819

[22] Filed: Feb. 22, 1996

[51] Int. Cl.[6] ..... A01H 5/00

[52] U.S. Cl. ..... Plt./82.4

[58] Field of Search ..... Plt./74.1, 82.4, Plt./82.3, 82.5

[56] References Cited

U.S. PATENT DOCUMENTS

P.P. 9,026 1/1995 VandenBerg ..... Plt./82.4
4,616,099 10/1986 Sparkes ..... 47/58

OTHER PUBLICATIONS

Broertjes, et al., 1980, "A mutant of a mutant of a . . . Irradiation of progressive radiation–induced mutants in a mutation breeding prgramme with *Chrysanthemum morifolium*", Euphytica, 29:525–530.

Gosling, ed., 1979, "The Chrysanthemum Manual–6th edition", The National Chrysanthemum Society, London, Essex Telegraph Press, Ltd., pp. 329–336.

Broertjes, et al., 1978 "Application of Mutation Breeding Methods in the Improvement of Vegetatively Propagated Crops"; Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by x– rays", Am. Soc. Hort. Sci. Proc., pp. 613–620.

Broertjes, 1966, "Mutation breeding of chrysanthemums", Euphytica, 15:156–162.

Dowrick, et al., 1966, "The induction of mutations in chrysanthemum using x–and gamma radiation", Euphytica, 15:204–210.

*Primary Examiner*—Howard J. Locker
*Attorney, Agent, or Firm*—Foley & Lardner

[57] ABSTRACT

A Chrysanthemum plant named Autumn Kimberly particularly characterized by its flat capitulum form; daisy capitulum type; greyed-red ray floret color; diameter across face of capitulum of 47 to 52 mm when fully opened; branching pattern is spreading and prolific, with 9 laterals developing after pinch when grown outside under natural daylength in fall flowerings; natural season flower date of September 2 to 7 when planting rooted cuttings on June 17 to 21 in Salinas, Calif., and of October 5 to 17 when planting rooted cuttings June 15 to 18 in Hightstown, N.J.; plant height of 30 to 36 cm when grown in fall under natural daylength with no growth regulators; and durable, uniform performance.

1 Drawing Sheet

The present invention comprises a new and distinct cultivar of Chrysanthemum, botanically known as *Dendranthema grandiflora*, and referred to by the cultivar name Autumn Kimberly.

Autumn Kimberly, identified as 7979 (89-707A02), is a product of a mutation induction program. The new cultivar was discovered and selected by inventor Leon Glicenstein on Sep. 1, 1993 in a controlled environment in Salinas, Calif. as one flowering plant within a flowering block established as rooted cuttings from stock plants which had been exposed as unrooted cuttings to an X-ray source of 2000 rads in Fort Myers, Fla. on Jan. 28, 1993. The irradiated parent cultivar was the cultivar Kimberly, disclosed in U.S. Plant Pat. No. 9,026 and described as a flat daisy garden mum with light purple flower color.

The irradiation program resulting in Autumn Kimberly had as its primary objective the expansion of color ranges of the parent cultivar Kimberly. The irradiation program comprised irradiation of cuttings of the parent cultivar at irradiation levels of 1500, 1750 and 2000 rads. A total of 986 cuttings harvested from a total of 225 irradiated plants were planted on Jun. 21, 1993. Of these, 13 initial selections were made, which selections were then revegetated and reflowered. Three consecutive flowerings resulted in discarding 6 of the original 13 selections on Apr. 18, 1994. The remaining 7 selections were maintained as PIs (Possible Introductions) and further trialed in Salinas, Calif., Hightstown, N.J. and Leamington, Ontario, Canada, ultimately resulting in discarding 5 selections on Oct. 17, 1994, and the decision to introduce one selection as Autumn Kimberly, and the other selection as Gentle Kimberly, disclosed in pending application Ser. No. 08/605,812.

The first act of asexual reproduction of Autumn Kimberly was accomplished when vegetative cuttings were taken from the initial selection in November of 1993 in a controlled environment in Salinas, Calif., by technicians working under supervision of Leon Glicenstein.

Horticultural examination of controlled flowerings of successive plantings has shown that the unique combination of characteristics as herein disclosed for Autumn Kimberly are firmly fixed and are retained through successive generations of asexual reproduction.

Autumn Kimberly has not been observed under all possible environmental conditions. The phenotype may vary significantly with variations in environment such as temperature, light intensity and daylength, without, however, any variance in genotype.

The following observations, measurements and comparisons described plants grown in controlled open areas in Salinas, Calif., and in Hightstown, N.J. Rooted cuttings were established in soil and maintained outdoors under the natural temperature and daylength prevailing during June through October.

The following traits have been repeatedly observed and are determined to be basic characteristics of Autumn Kimberly, which, in combination, distinguish this Chrysanthemum as a new and distinct cultivar:

1. Flat capitulum form.
2. Daisy capitulum type.
3. Greyed-red ray floret color.
4. Diameter across face of capitulum of 47 to 52 mm when fully opened.
5. Branching pattern is spreading and prolific, with 9 laterals developing after pinch when grown outside under natural daylength in fall flowerings.
6. Natural season flower date of September 2 to 7 when planting rooted cuttings on June 17 to 21 in Salinas, Calif., and of October 5 to 17 when planting rooted cuttings June 15 to 18 in Hightstown, N.J.

7. Plant height of 30 to 36 cm when grown in fall under natural daylength with no growth regulators.

8 Durable, uniform performance.

The accompanying photographic drawing is a color photograph of Autumn Kimberly grown as a pinched garden mum under natural season outside conditions in Salinas, Calif., with the colors being as nearly true as possible with illustrations of this type. Plants were grown outside and dug and transplanted into 15 cm pots at flowering time for photography purposes.

Of the commercial cultivars known to the inventor, the most similar in comparison to Autumn Kimberly is the parent cultivar Kimberly. All traits of Autumn Kimberly are similar to those of Kimberly, except for the ray floret color. The ray floret color of Autumn Kimberly is greyed-red (RHS 181B to 181C), while the ray floret color of Kimberly is light purple (RHS 75B to 75C). Autumn Kimberly similarly differs from sibling cultivar Gentle Kimberly only with respect to ray floret color.

In the following description color references are made to The Royal Horticultural Society Colour Chart. The color values were determined on plant material grown as a pinched garden mum grown outdoors in Salinas, Calif. on Sep. 1, 1995.

Classification:

*Botanical.*—*Dendranthema grandiflora* cv Autumn Kimberly.

*Commercial.*—Flat daisy garden mum.

INFLORESCENCE

A. Capitulum:

*Form.*—Flat

*Type.*—Daisy.

*Diameter across face.*—47 to 52 mm when fully opened.

B. Corolla of ray florets:

*Color (general tonality from a distance of three meters)* .—Greyed-red.

*Color (upper surface).*—181B to 181C.

*Color (under surface).*—182B.

*Shape.*—Cross-section flat, longitudinal section straigh. Ray floret tips rounded.

C. Corolla of disc florets:

*Color (Mature).*—17C.

*Color (immature).*—14A, tinged wtih 144C.

D. Reproductive organs

*Androecium.*—Present on disc florets only; moderate pollen.

*Gynoecium.*—Present on both ray and disc florets.

PLANT

A. General appearance:

*Height.*—30 to 36 cm when grown in fall under natural daylength with no growth regulators.

*Branching pattern.*—Spreading and prolific, with 9 laterals developing after pinch when grown outside under natural daylength in fall flowerings.

B. Foliage:

*Color (upper surface).*—147A.

*Color (under surface).*—147B.

*Shape.*—Amall, lobed, slightly serrated.

What is claimed is:

1. A new and distinct Chrysanthemum plant named Autumn Kimberly, as described and illustrated.

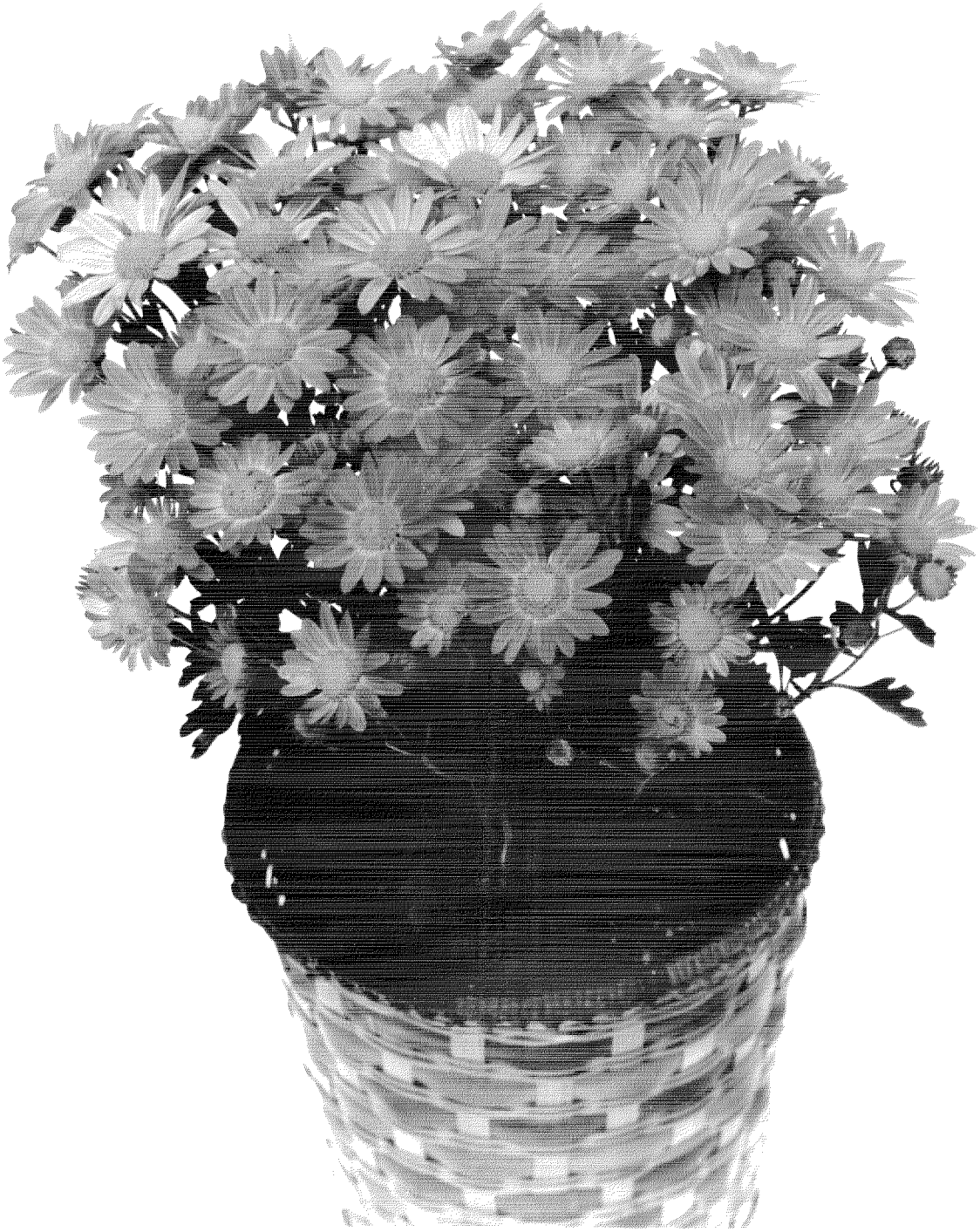

* * * * *